US008889837B2

(12) United States Patent
Burg et al.

(10) Patent No.: US 8,889,837 B2
(45) Date of Patent: *Nov. 18, 2014

(54) PURIFICATION OF PEGYLATED POLYPEPTIDES

(75) Inventors: Josef Burg, Weilheim (DE); Klaus Reichert, Oberhausen (DE); Axel Schroth, Sindelsdorf (DE); Hartmut Schurig, Loerrach (DE); Axel Wessner, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 144 days.

This patent is subject to a terminal disclaimer.

(21) Appl. No.: 12/931,070

(22) Filed: Jan. 24, 2011

(65) Prior Publication Data

US 2011/0118448 A1 May 19, 2011

Related U.S. Application Data

(63) Continuation of application No. 12/218,545, filed on Jul. 16, 2008, now Pat. No. 8,138,317.

(30) Foreign Application Priority Data

Jul. 17, 2007 (EP) ..................... 07013959

(51) Int. Cl.
| | |
|---|---|
| C07K 1/14 | (2006.01) |
| C07K 1/16 | (2006.01) |
| C07K 1/18 | (2006.01) |
| C07K 1/22 | (2006.01) |
| C07K 14/505 | (2006.01) |
| A61K 47/48 | (2006.01) |

(52) U.S. Cl.
CPC ............. *C07K 1/18* (2013.01); *A61K 47/48215* (2013.01); *C07K 14/505* (2013.01)
USPC ........... 530/413; 530/397; 530/402; 530/416; 530/417; 530/421

(58) Field of Classification Search
None
See application file for complete search history.

(56) References Cited

U.S. PATENT DOCUMENTS

| | | |
|---|---|---|
| 5,118,796 A | 6/1992 | Prior et al. |
| 5,183,660 A | 2/1993 | Ikeda et al. |
| 5,234,878 A | 8/1993 | Tsutsui et al. |
| 5,264,209 A | 11/1993 | Mikayama et al. |
| 5,264,555 A | 11/1993 | Shorr et al. |
| 5,635,371 A | 6/1997 | Stout et al. |
| 5,641,670 A | 6/1997 | Treco et al. |
| 5,733,746 | 3/1998 | Treco et al. |
| 5,733,761 A | 3/1998 | Treco et al. |
| 5,876,969 A | 3/1999 | Fleer et al. |
| 5,932,462 A | 8/1999 | Harris et al. |
| 5,932,463 A | 8/1999 | Asakura et al. |
| 6,120,761 A | 9/2000 | Yamazaki et al. |
| 6,333,306 B1 | 12/2001 | Lehmann |
| 6,372,715 B1 | 4/2002 | Kaltwasser et al. |
| 6,399,333 B1 | 6/2002 | Burg et al. |
| 6,440,932 B1 | 8/2002 | Lehmann et al. |
| 6,528,314 B1 | 3/2003 | Le Mouellic et al. |
| 6,583,272 B1* | 6/2003 | Bailon .......................... 530/397 |
| 6,583,273 B1 | 6/2003 | Bacher et al. |
| 6,930,086 B2 | 8/2005 | Tischer |
| 7,012,130 B1 | 3/2006 | Carcagno et al. |
| 7,169,754 B2 | 1/2007 | Papadimitriou |
| 7,202,208 B2 | 4/2007 | Papadimitriou |
| 7,262,166 B2 | 8/2007 | Kinstler et al. |
| 7,294,615 B1 | 11/2007 | Bovin et al. |
| 7,351,801 B2 | 4/2008 | Belew |
| 7,494,972 B2 | 2/2009 | Stern et al. |
| 7,759,092 B2 | 7/2010 | Zamost et al. |
| 7,846,336 B2 | 12/2010 | Burg et al. |
| 8,138,317 B2* | 3/2012 | Burg et al. .................... 530/412 |
| 2002/0115833 A1* | 8/2002 | Burg et al. .................... 530/395 |
| 2002/0147311 A1 | 10/2002 | Gillies et al. |
| 2003/0148005 A1 | 8/2003 | Chang et al. |
| 2004/0106747 A1* | 6/2004 | Bailon et al. .................. 525/418 |
| 2004/0147431 A1* | 7/2004 | Papadimitriou .................. 514/8 |
| 2005/0008649 A1 | 1/2005 | Shin et al. |
| 2005/0100991 A1 | 5/2005 | Rosen et al. |
| 2005/0114037 A1 | 5/2005 | Desjarlais et al. |
| 2006/0189529 A1* | 8/2006 | Cho et al. ....................... 514/12 |
| 2006/0264377 A1 | 11/2006 | Kinstler et al. |
| 2008/0230478 A1 | 9/2008 | Johansson et al. |
| 2009/0098660 A1 | 4/2009 | Falkenstein et al. |
| 2009/0101585 A1 | 4/2009 | Burg et al. |
| 2010/0267632 A1 | 10/2010 | Haselbeck et al. |

FOREIGN PATENT DOCUMENTS

| | | |
|---|---|---|
| CL | 2053-2007 A1 | 6/2008 |
| EP | 0 530 447 A2 | 3/1993 |
| EP | 0 583 447 A1 | 2/1994 |
| EP | 0 442 725 B1 | 10/1995 |

(Continued)

OTHER PUBLICATIONS

Roe, Simon, 2001, "Protein Purification Techniques," Oxford University Press. London.*
Havugimana, et al, 2007, Improved proteomic discovery by sample pre-fractionation using dual-column ion-exchange high performance liquid chromatography. J. Chromatog., 847: 54-61.*
Bristow, A. "Collaborative Study for the Establishment of a Biological Reference Preparation for Erythropoietin", PHARMEUROPA Spec. Issue, BIO 2 (1997) pp. 31-49.
Delgado, et al. "The Uses and Properties of PEG-Linked Proteins", *Critical Reviews in Therapeutic Drug Carrier Syst.* 9 (3,4) (1992), pp. 249-304.
Felix, A.M. Site-Specific Poly(ethylene glycol)ylation of Peptides, *Amer. Chem, Soc.* Symp. Ser. 680 (1997), pp. 218-238.
Francis, et al. "PEGylation of cytokines and other therapeutic proteins and peptides: the importance of biological optimization of coupling techniques", *Int. J. Hematol.* 68 (1998), pp. 1-18.

(Continued)

*Primary Examiner* — Elizabeth C Kemmerer
*Assistant Examiner* — Regina M Deberry
(74) *Attorney, Agent, or Firm* — Fulbright & Jaworski LLP (57) ABSTRACT

The invention is a method for the purification of mono-PEGylated erythropoietin using two cation exchange chromatography steps wherein the same type of cation exchange material is used in both cation exchange chromatography steps and a method for producing a mono-PEGylated erythropoietin in substantially homogeneous form.

18 Claims, 3 Drawing Sheets

(56) References Cited

FOREIGN PATENT DOCUMENTS

| EP | 0 473 084 B1 | 11/1995 |
|---|---|---|
| EP | 0 442 724 B1 | 10/1999 |
| EP | 1 064 951 | 8/2007 |
| JP | 2001-064300 A | 3/2001 |
| JP | 2005-538176 A | 12/2005 |
| JP | 2006-512283 A | 4/2006 |
| WO | WO 89/05157 A1 | 6/1989 |
| WO | WO 90/11354 | 10/1990 |
| WO | WO 91/06667 | 5/1991 |
| WO | WO 91/09955 A1 | 7/1991 |
| WO | WO 91/09956 A1 | 7/1991 |
| WO | WO 93/09222 | 5/1993 |
| WO | WO 93/17583 A1 | 9/1993 |
| WO | WO 94/01451 A2 | 1/1994 |
| WO | WO 94/01452 | 1/1994 |
| WO | WO 94/12650 | 6/1994 |
| WO | WO 95/31560 | 11/1995 |
| WO | WO 96/35718 A1 | 11/1996 |
| WO | WO 97/09996 | 3/1997 |
| WO | WO 97/40850 A1 | 11/1997 |
| WO | WO 98/58660 | 12/1998 |
| WO | WO 98/58661 | 12/1998 |
| WO | WO 99/07401 A2 | 2/1999 |
| WO | WO 99/07402 | 2/1999 |
| WO | WO 00/27869 A1 | 5/2000 |
| WO | WO 00/44785 | 8/2000 |
| WO | WO 00/44786 | 8/2000 |
| WO | WO 01/02017 A2 | 1/2001 |
| WO | WO 01/02018 A2 | 1/2001 |
| WO | WO 01/76640 A2 | 10/2001 |
| WO | WO 01/87329 A1 | 11/2001 |
| WO | WO 03/029291 A2 | 4/2003 |
| WO | WO 03/097693 A1 | 11/2003 |
| WO | WO 2004/009627 A1 | 1/2004 |
| WO | WO 2004/012773 A1 | 2/2004 |
| WO | WO 2004/024866 A2 | 3/2004 |
| WO | WO 2006/011839 A1 | 2/2006 |
| WO | WO 2006/125599 A2 | 11/2006 |
| WO | WO 2007/039436 A1 | 4/2007 |
| WO | WO 2007/041713 A1 | 4/2007 |
| WO | WO 2008/010061 A2 | 1/2008 |
| WO | WO 2009/010271 A2 | 1/2009 |

OTHER PUBLICATIONS

Hermanson, G.T., in Bioconjugate Techniques, Academic Press, San Diego (1996), pp. 147-148.

Long, et al. "Design of homogeneous, monopegylated erythropoietin analogs with preserved in vitro bioactivity", *Experim. Hematol.* 34 (2006), pp. 697-704.

Morpurgo, et al. Preparation and Characterization of Poly((ethylene glycol) Vinyl Sulfone, *Bioconjugate Chem.*, 7 (1996), pp. 363-368.

Veronese, F.M. "Peptide and protein PEGylation: a review of problems and solutions", *Biomater.* 22 (2001), pp. 405-417.

Bioworld Online Catalog, http://www.bio-world.com/productioninfo/2_18_162_670/1187/Blue-sepharose-CL-B.html.

Danielsoon, et al. "One-step purification of monoclonal IgG antibodies from mouse ascites", *J. Immunol. Meth.*, 115 (1988) pp. 79-88.

Lu, et al. "Pegylated peptides. III. Solid-phase synthesis with pegylating reagents of varying molecular weight: synthesis of multiply pegylated peptides", *Readtive Polymers*, 22 (1994), pp. 221-229.

Monfardini, et al. "A Branched Monomethoxypoly(ethylene glycol) for Protein Modification", *Bioconjugate Chem.* 6 (1995), pp. 62-69.

Necina, et al. "Capture of Human Monoclonal Antibodies from Cell Culture Supernatant by Ion Exchange Media Exhibiting High Charge Density", *Biotechnol. Bioeng.* 60 (1998) pp. 689-698.

Vijayalakshmi M.A. "Antibody Purification Methods", *Applied Biochem. Biotechnol.* 75 (1998), pp. 93-103.

Wang, et al. "High-level expression of human TFF3 in *Escherichia coil*", *Peptides* 26 (2005) pp. 1213-1218.

Yu, et al. "Facile purification of mono-PEGylated interleukin-1 receptor antagonist and its characterization with multi-angle laser light scattering", *Process Biochem.* 42 (2007), pp. 971-977.

Yun, et al. "Reproducible preparation and effective separation of PEGylated recombinant human granulocyte colony-stimulating factor with novel "PEG-pellet" PEGylation mode and ion-exchange chromatography", *J. Biotechlog.*, 118 (2005), pp. 67-74.

"Tanpakushitsu Jikken Note" (Handbook for Protein Experimentation), vol. 1, Publ. by Yodosha Co., Ltd.(1996); English translation of relevant part, p. 1-12.

Current Protocols in Molecular Biology, Unit 10.10 Ion-Exchange Chromatography, John Wiley & Sons, Inc. (1998), p. 10.10.1-10.10.30.

Current Protocols in Protein Science, Unit 8.2 Ion-Exchange Chromatography, John Wiley & Sons, Inc. (1999), p. 8.2.1-8.2.30.

Goding, W. James "Monoclonal Antibodies Principles and Practice" (1986), Section 4.2.4 Non-Exchange Chromatography, $2^{nd}$ Edition; Academic Press, p. 110-117.

Ion-Exchange Chromatography: Principles and Methods, (1994), Pharmacia Biotech, p. 1-4.

* cited by examiner

SEQUENCE LISTING

<160> NUMBER OF SEQ ID NOS: 2

<210> SEQ ID NO 1
<211> LENGTH: 165
<212> TYPE: PRT

-continued

```
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

PURIFICATION OF PEGYLATED POLYPEPTIDES

PRIORITY TO RELATED APPLICATION(S)

This application is a continuation of application Ser. No. 12/218,545 filed Jul. 16, 2008, now U.S. Pat. No. 8,138,317 which claims the benefit of European Patent Application No. 07013959.7, filed Jul. 17, 2007, which is hereby incorporated by reference in its entirety.

The current invention relates to chromatographic separation methods useful for the purification of polypeptides, especially of PEGylated erythropoietin.

BACKGROUND AND PRIOR ART

Proteins play an important role in today's medical portfolio. For human applications every therapeutic protein has to meet distinct criteria. To ensure the safety of biopharmaceutical agents to humans, it is especially important that by-products which accumulate during production processes be removed. To fulfill regulatory specifications, one or more purification steps have to follow the manufacturing process. Among other things, purity, throughput, and yield play important roles in determining an appropriate purification process.

Different methods are well established and their use for protein purification is widespread, such as affinity chromatography with microbial proteins (e.g., protein A and protein G affinity chromatography), ion exchange chromatography (e.g., cation exchange (sulfopropyl or carboxymethyl resins), anion exchange (amino ethyl resins and mixed-mode ion exchange), thiophilic adsorption (e.g., with beta-mercaptoethanol and other SH ligands), hydrophobic interaction or aromatic adsorption chromatography (e.g., with phenyl-sepharose, aza-arenophilic resins, or m-aminophenylboronic acid), metal chelate affinity chromatography (e.g., with Ni(II)- and Cu(II)-affinity material), size exclusion chromatography, and electrophoretical methods (such as gel electrophoresis, and capillary electrophoresis) (Vijayalakshmi, M. A., Appl. Biochem. Biotech. 75 (1998) 93-102)).

Conjugates of polyethylene glycol (PEG) and, e.g., Interleukin-6 (EP 0 442 724), erythropoietin (WO 01/02017), chimeric molecules comprising Endostatin and immunoglobulins (US 2005/008649), secreted antibody based fusion proteins (US 2002/147311), fusion polypeptides comprising albumin (US 2005/0100991, human serum albumin U.S. Pat. No. 5,876,969), PEGylated polypeptides (US 2005/0114037), and for interferon fusions have been reported.

Necina, R., et al. (Biotechnol. Bioeng. 60 (1998) 689-698) reported the capture of human monoclonal antibodies directly from cell culture supernatants by ion exchange media exhibiting high charge density. In WO 89/05157 a method is reported for the purification of immunoglobulins by directly subjecting the cell culture medium to cation exchange treatment. One-step purification of monoclonal IgG antibodies from mouse ascites is described by Danielsson, A., et al., J. Immun. Meth. 115 (1988), 79-88. A method for purifying a polypeptide by ion exchange chromatography is reported in WO 2004/024866 in which a gradient wash is used to resolve a polypeptide of interest from one or more contaminants. In EP 0 530 447 a process for purifying IgG monoclonal antibodies by a combination of three chromatographic steps is reported. A facile purification of mono-PEGylated interleukin-1 receptor antagonist is reported by Yu, G., et al., in Process Biotechnol. 42 (2007) 971-977. Wang et al. (Wang, H., et al., Peptides 26 (2005) 1213-1218) reports the purification of hTFF3 expressed in *E. coli* by two step cation exchange chromatography. Yun et al. (Yun, Q., et al., J. Biotechnol. 118 (2005) 67-74) report the purification of PEGylated rhG-CSF by two consecutive ion-exchange chromatography steps. WO 2007/039436 and WO 01/087329 report erythropoietin being covalently linked to poly (ethylene glycol) group(s) and a liquid pharmaceutical composition comprising an erythropoietin protein.

SUMMARY OF THE INVENTION

The current invention comprises a method for the purification of a mono-PEGylated erythropoietin comprising the steps of providing a solution comprising mono-, poly-, and non-PEGylated erythropoietin, performing two consecutive cation exchange chromatography steps, and recovering the purified mono-PEGylated erythropoietin in the second cation exchange chromatography step, wherein the same type of cation exchange material is used in both cation exchange chromatography steps.

In one embodiment of the method the two consecutive cation exchange chromatography steps are performed using different elution methods. In another embodiment the two consecutive cation exchange chromatography steps comprise the following steps:
a) applying an aqueous, buffered solution comprising a mixture of mono-, poly-, and non-PEGylated erythropoietin to a first cation exchange chromatography column under conditions suitable for binding of said mono-PEGylated erythropoietin to the cation exchange material contained in said first column,
b) recovering the mono-PEGylated erythropoietin from the first cation exchange chromatography column by a step elution method with a stepwise increase of the ionic strength of the flow through buffer, wherein the fraction of said mono-PEGylated erythropoietin is increased compared to the applied mixture of step a),
c) applying the recovered mono-PEGylated erythropoietin to a second cation exchange chromatography column under conditions suitable for binding of said mono-PEGylated erythropoietin to the cation exchange material contained in said second column, whereby the cation exchange material contained in said second column is of the same type as the cation exchange material in the first column,
d) recovering the purified mono-PEGylated erythropoietin in a substantially homogeneous form from said second cation exchange chromatography column by a continuous elution method with a continuous increase of the ionic strength of the through flowing buffer.

In one embodiment of the invention the cation exchange material is a strong cation exchange material. In a preferred embodiment the strong cation exchange material is a sulfopropyl cation exchange material. Especially preferred is Toyopearl® SP 650M. In another embodiment the mono-PEGylated erythropoietin is recovered in step d) in a substantially homogeneous form of more than 95 area % purity. In a further embodiment of the method the stepwise increase of the ionic strength in step b) of the method is a two step ionic strength increase. Preferably the mono-PEGylated erythropoietin is recovered in the second step of the step elution method, i.e., after the second increase in the ionic strength.

Another aspect of the current invention is a method for the production of a mono-PEGylated erythropoietin comprising the following steps:
a) PEGylating erythropoietin by using a PEGylating reagent,
b) purifying the PEGylated erythropoietin with two consecutive cation exchange chromatography steps, wherein the first and second cation exchange chromatography employ the same type of cation exchange material, c) recovering the mono-PEGylated erythropoietin from the second cation exchange chromatography column in a substantially homogeneous form.

DETAILED DESCRIPTION OF THE PREFERRED EMBODIMENTS

The current invention comprises a method for the purification of a mono-PEGylated erythropoietin comprising two cation exchange chromatography steps wherein the same type of cation exchange material is used in both cation exchange chromatography steps.

The term "ion exchange material" as used within this application denotes an immobile high molecular weight matrix that carries covalently bound charged substituents used as stationary phase in ion exchange chromatography. For overall charge neutrality, non-covalently bound counter ions are bound thereto. The "ion exchange material" has the ability to exchange its non-covalently bound counter ions for similarly charged ions of the surrounding solution. Depending on the charge of its exchangeable counter ions the "ion exchange resin" is referred to as cation exchange resin or as anion exchange resin. Depending on the nature of the charged group (substituent) the "ion exchange resin" is referred to as, e.g., in the case of cation exchange resins, sulfonic acid resin (S), or sulfopropyl resin (SP), or carboxymethyl resin (CM). Depending on the chemical nature of the charged group/substituent the "ion exchange resin" can additionally be classified as a strong or weak ion exchange resin, depending on the strength of the covalently bound charged substituent. For example, strong cation exchange resins have a sulfonic acid group, preferably a sulfopropyl group, as charged substituent, weak cation exchange resins have a carboxylic group, preferably a carboxymethyl group, as charged substituent, and weak anion exchange resins have a diethylaminoethyl group as charged substituent.

Different types of ion exchange materials, i.e., stationary phases, are available under different names and from a multitude of companies such as, e.g., cation exchange materials Bio-Rex® (e.g., type 70), Chelex® (e.g. type 100), Macro-Prep® (e.g., type CM, High S, 25 S), AG® (e.g., type 50W, MP) all available from BioRad Laboratories, WCX 2 available from Ciphergen, Dowex® MAC-3 available from Dow chemical company, Mustang C and Mustang S available from Pall Corporation, Cellulose CM (e.g., type 23, 52), hyper-D, partisphere available from Whatman plc., Amberlite® IRC (e.g., type 76, 747, 748), Amberlite® GT 73, Toyopearl® (e.g., type SP, CM, 650M) all available from Tosoh Bioscience GmbH, CM 1500 and CM 3000 available from Bio-Chrom Labs, SP-Sepharose™, CM-Sepharose™ available from GE Healthcare, Porous resins available from PerSeptive Biosystems, Asahipak ES (e.g., type 502C), CXpak P, IEC CM (e.g., type 825, 2825, 5025, LG), MC SP (e.g., type 420N, 825), IEC QA (e.g., type LG, 825) available from Shoko America Inc., 50W cation exchange resin available from Eichrom Technologies Inc. Preferably the cation exchange material is a strong cation exchange material such as Macro-Prep® High S or 25S, MacroCap SP, Toyopearl® SP 650M, Source S, SP Sepharose, or POLYCAT A. Exemplary anion exchange materials are Dowex® 1 available from Dow chemical company, AG® (e.g., type 1, 2, 4), Bio-Rex® 5, DEAE Bio-Gel 1, Macro-Prep® DEAE all available from BioRad Laboratories, anion exchange resin type 1 available from Eichrom Technologies Inc., Source Q, ANX Sepharose 4, DEAE Sepharose (e.g., type CL-6B, FF), Q Sepharose, Capto Q, Capto S all available from GE Healthcare, AX-300 available from PerkinElmer, Asahipak ES-502C, AXpak WA (e.g., type 624, G), IEC DEAE all available from Shoko America Inc., Amberlite® IRA-96, Toyopearl® DEAE, TSKgel DEAE all available from Tosoh Bioscience GmbH, Mustang Q available from Pall Corporation. In one embodiment the cation exchange material is a sulfopropyl cation exchange material.

The term "same type of cation exchange material" denotes two consecutive ion exchange chromatography steps which are performed by employing an identical cation exchange material. This means that the consecutive cation exchange chromatography steps are carried out by using either a first portion of the cation exchange material for the first cation exchange chromatography step and by using a second portion of the same cation exchange material for the second cation exchange chromatography step or by using the same cation exchange material for both cation exchange chromatography steps. In one embodiment the second cation exchange material is the same type of cation exchange material but not the same fraction of the cation exchange material as the first cation exchange material.

The terms "step elution" and "step elution method", which are used interchangeably within this application, denote a method wherein, e.g., the concentration of a substance causing elution, i.e., the dissolution of a bound compound from a material, is raised or lowered at once, i.e., directly from one value/level to the next value/level. In this "step elution" one or more conditions, for example the pH, the ionic strength, concentration of a salt, and/or the flow of a chromatography, is/are changed all at once from a first, e.g., starting, value to a second, e.g., final, value, i.e., the conditions are changed incrementally, i.e., stepwise, in contrast to a linear change. In the "step elution method" after each increase in the ionic strength a new fraction is collected. This fraction contains the compounds recovered from the ion exchange material with a corresponding increase in ionic strength. After each increase the conditions are maintained until the next step in the elution method. In "step elution" one or more conditions is/are changed all at once from a first, e.g., starting, value to a second, e.g., final, value. The change in one embodiment is 10% or more of the concentration of the substance causing elution. That is in this embodiment, the concentration of the substance causing elution is 100% in the first step, 110% or more in the second step, and 120% or more in the third step. In another embodiment the change is 50% or more of the concentration of the substance causing elution. In another embodiment the change is 120% or more of the concentration of the substance causing elution. "Step elution" denotes that the conditions are changed incrementally, i.e., stepwise, in contrast to a linear change.

The terms "continuous elution" and "continuous elution method", which are used interchangeably within this application, denote a method wherein, e.g., the concentration of a substance causing elution, i.e., the dissolution of a bound/adsorbed compound from a chromatographic material, is raised or lowered continuously, i.e., the concentration is changed by a sequence of small steps each not bigger than a change of 2%, preferably of 1% of the concentration of the substance causing elution. In this "continuous elution" one or more conditions, for example the pH, the ionic strength, concentration of a salt, and/or the flow of a chromatography, may be changed linearly or exponentially or asymptotically. Preferably the change is linear.

The term "applying to" and grammatical equivalents thereof as used within this application denotes a partial step of a purification method in which a solution containing a substance of interest to be purified is brought in contact with a stationary phase. This denotes that a) the solution is added to a chromatographic device in which the stationary phase is located, or b) that a stationary phase is added to the solution. In case a) the solution containing the substance of interest to be purified passes through the stationary phase allowing for an interaction between the stationary phase and the substances in solution. Depending on the conditions, such as, e.g., pH, conductivity, salt concentration, temperature, and/or flow rate, some substances of the solution are bound to the stationary phase and thus are removed from the solution. Other substances remain in solution. The substances remaining in solution can be found in the flow-through. The "flow-through" denotes the solution obtained after the passage of the chromatographic device, which may either be the applied solution containing the substance of interest or the buffer, which is used to flush the column or to cause elution of one or more substances bound to the stationary phase. In one embodiment the chromatographic device is a column, or a cassette. The substance of interest can be recovered from the solution after the purification step by methods familiar to a person of skill in the art, such as, e.g., precipitation, salting out, ultrafiltration, diafiltration, lyophilization, affinity chromatography, or solvent volume reduction to obtain the substance of interest in substantially homogeneous form. In case b) the stationary phase is added, e.g., as a solid, to the solution containing the substance of interest to be purified allowing for an interaction between the stationary phase and the substances in solution. After the interaction the stationary phase is removed, e.g., by filtration, and the substance of interest is either bound to the stationary phase and removed therewith from the solution or not bound to the stationary phase and remains in the solution.

The term "under conditions suitable for binding" and grammatical equivalents thereof as used within this application denotes that a substance of interest, e.g., PEGylated erythropoietin, binds to a stationary phase when brought in contact with it, e.g., an ion exchange material. This does not necessarily mean that 100% of the substance of interest is bound but essentially 100% of the substance of interest is bound, i.e., at least 50% of the substance of interest is bound, more preferably at least 75% of the substance of interest is bound, even more preferably at least 85% of the substance of interest is bound, and especially preferably more than 95% of the substance of interest is bound to the stationary phase.

The term "buffered" as used within this application denotes a solution in which changes of pH due to the addition or release of acidic or basic substances is leveled by a buffer substance. Any buffer substance resulting in such an effect can be used. Preferably pharmaceutically acceptable buffer substances are used, such as, e.g., phosphoric acid or salts thereof, acetic acid or salts thereof, citric acid or salts thereof, morpholine, 2-(N-morpholino)ethanesulfonic acid or salts thereof, histidine or salts thereof, glycine or salts thereof, or tris (hydroxymethyl)aminomethane (TRIS) or salts thereof. In one embodiment phosphoric acid or salts thereof, or acetic acid or salts thereof, or citric acid or salts thereof, or histidine or salts thereof are used as the buffer substance. Optionally the buffered solution may comprise an additional salt, such as, e.g., sodium chloride, sodium sulphate, potassium chloride, potassium sulfate, sodium citrate, or potassium citrate.

General chromatographic methods and their use are known to a person skilled in the art. See for example, Chromatography, 5$^{th}$ edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

The PEGylation of erythropoietin normally results in a mixture of different compounds, such as poly-PEGylated erythropoietin, mono-PEGylated erythropoietin, non-PEGylated erythropoietin, hydrolysis products of the activated PEG ester, e.g., the free PEGylated acid, as well as hydrolysis products of the erythropoietin itself. In order to obtain a mono-PEGylated erythropoietin in substantially homogeneous form, these substances have to be separated and the compound of interest has to be purified.

Therefore, it is an aspect of the current invention to provide a method for obtaining a mono-PEGylated erythropoietin in substantially homogenous form comprising the following steps:
a) PEGylating erythropoietin using an activated PEGylating reagent having a molecular weight of from 20 kDa to 40 kDa,
b) purifying the PEGylated erythropoietin obtained in step a) with two consecutive cation exchange chromatography steps, wherein the first and second cation exchange chromatography steps employ the same type of cation exchange material,
c) recovering the mono-PEGylated erythropoietin from the second cation exchange chromatography column in substantially homogeneous form.

This method is especially useful for the purification of PEGylated recombinant polypeptides, which are glycosylated, i.e., which have been produced by a mammalian cell, preferably a CHO cell, HEK293 cell, BHK cell, Per.C6® cell, or HeLa cell and are afterwards chemically PEGylated.

In the first step of the method the erythropoietin is PEGylated. The poly(ethylene glycol) (PEG) polymer molecules used in the PEGylation reaction have a molecular weight of about 20 kDa to 40 kDa (by "molecular weight" as used herein there is to be understood the mean molecular weight of the PEG because PEG as a polymeric compound is not obtained with a defined molecular weight but in fact has a molecular weight distribution; the term "about" indicates that in said PEG preparations, some molecules will weigh more and some less than the indicated molecular weight, i.e. the term about refers to a molecular weight distribution in which 95% of the PEG molecules have a molecular weight within +/−10% of the indicated molecular weight. For example, a molecular weight of 30 kDa denotes a range of from 27 kDa to 33 kDa).

The term "erythropoietin" refers to a protein having the sequence SEQ ID NO:1 or SEQ ID NO:2, or a protein or polypeptide substantially homologous thereto, whose biological properties relate to the stimulation of red blood cell production and the stimulation of the division and differentiation of committed erythroid progenitors in the bone marrow. Recombinant erythropoietin may be prepared via expression in eukaryotic cells, for example in CHO cells, BHK cells, or HeLa cells by recombinant DNA technology or by endogenous gene activation. For example the erythropoietin glycoprotein may be expressed by endogenous gene activation as reported in U.S. Pat. Nos. 5,733,761, 5,641,670, 5,733,746, WO 93/09222, WO 94/12650, WO 95/31560, WO 90/11354, WO 91/06667, and WO 91/09955. In one embodiment the erythropoietin according to the invention is based on the sequence of human EPO. In another embodiment the human erythropoietin has the amino acid sequence set out in SEQ ID NO: 1 or SEQ ID NO: 2. Preferably the human erythropoietin has the amino acid sequence set out in SEQ ID NO: 1. The term "erythropoietin" also denotes variants of the protein of SEQ ID NO: 1 or SEQ ID NO: 2, in which one or more amino acid residues have been changed, deleted, or inserted, and which has the same biological activity as the non-modified protein, such as, e.g., reported in EP 1 064 951, or U.S. Pat. No. 6,583,272. A variant may have the amino acid sequence of human erythropoietin having from 1 to 6 additional sites for glycosylation. The specific activity of PEGylated erythropoietin can be determined by various assays known in the art. The biological activity of the purified PEGylated erythropoietin of this invention are such that administration of the protein by injection to human patients results in bone marrow cells increasing production of reticulocytes and red blood cells as compared to non-injected or control groups of subjects. The biological activity of the PEGylated erythropoietin obtained and purified in accordance with this invention can be tested by methods according to Pharm. Europa Spec. Issue Erythropoietin BRP Bio 1997(2).

"PEG" or "PEG group" according to the invention means a residue containing poly (ethylene glycol) as an essential part. Such a PEG can contain further chemical groups which are necessary for binding, i.e., conjugation, reactions, which result from the chemical synthesis of the molecule, or which is a spacer for optimal distance of parts of the molecule. These further chemical groups are not used for the calculation of the molecular weight of the PEG polymer molecule. In addition, such a PEG can consist of one or more PEG side-chains, which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. Branched PEGs are described, for example, in EP 0 473 084, and U.S. Pat. No. 5,932,462. In preferred embodiments a PEG with a molecular weight of 20-35 kDa linear PEG molecules is used and branched PEG polymers with a molecular weight of more than 35 kDa, especially with 40 kDa, are used. In one embodiment, a two-armed, 40 kDa PEG is used.

The term "PEGylation" means a covalent linkage of a poly (ethylene glycol) residue at the N-terminus of the polypeptide and/or an internal lysine residue. PEGylation of proteins is widely known in the state of the art and is reviewed by, for example, Veronese, F. M., Biomaterials 22 (2001) 405-417. PEG can be linked using different functional groups and polyethylene glycols with different molecular weight, linear and branched PEGs as well as different linking groups (see also Francis, G. E., et al., Int. J. Hematol. 68 (1998) 1-18; Delgado, C., et al., Crit. Rev. Ther. Drug Carrier Systems 9 (1992) 249-304). PEGylation of erythropoietin can be performed in aqueous solution with PEGylation reagents as described, for example, in WO 00/44785, by using NHS-activated linear or branched PEG molecules of a molecular weight between 5 kDa and 40 kDa. PEGylation can also be performed at the solid phase according to Lu, Y., et al., Reactive Polymers 22 (1994) 221-229. Not randomly, N-terminally PEGylated polypeptide can also be produced according to WO 94/01451.

Such methods result in an erythropoietin which is PEGylated at one or more ε-amino groups of lysine residues and/or at the N-terminal amino group. Selective PEGylation at the N-terminal amino acid can be performed according to Felix, A. M., et al., ACS Symp. Ser. 680 (Poly(ethylene glycol)) (1997) 218-238. Selective N-terminal PEGylation can be achieved during solid-phase synthesis by coupling of a $N^\alpha$-PEGylated amino acid derivative to the N-1 terminal amino acid of the peptide chain. Side chain PEGylation can be performed during solid-phase synthesis by coupling of $N^\epsilon$-PEGylated lysine derivatives to the growing chain. Combined N-terminal and side chain PEGylation is feasible either as described above within solid-phase synthesis or by solution phase synthesis by applying activated PEG reagents to an amino deprotected peptide.

Suitable PEG derivatives are activated PEG molecules with an average molecular weight of from about 5 to about 40 kDa, in one embodiment from about 20 to about 40 kDa, preferably about 30 kDa to about 35 kDa. The PEG derivative is in one embodiment a linear or a branched PEG. A wide variety of PEG derivatives suitable for use in the preparation of PEG-protein and PEG-peptide conjugates can be obtained from Shearwater Polymers (Huntsville, Ala., U.S.A.; www.nektar.com).

Activated PEG derivatives are known in the art and are described in, for example, Morpurgo, M., et al., J. Bioconjug. Chem. 7 (1996) 363-368, for PEG-vinylsulfone. Linear chain and branched chain PEG species are suitable for the preparation of the PEGylated fragments. Examples of reactive PEG reagents are iodo-acetyl-methoxy-PEG, or methoxy-PEG-vinylsulfone (m is preferably an integer from about 450 to about 900 and R is a $C_1$- to $C_6$-alkyl, linear or branched, having one to six carbon atoms such as methyl, ethyl, isopropyl, etc. whereby in one embodiment R=methyl):

The use of these iodo-activated substances is known in the art and described, e.g., by Hermanson, G. T., in Bioconjugate Techniques, Academic Press, San Diego (1996) p. 147-148.

In one embodiment the PEG species is an activated PEG ester, e.g., N-hydroxysuccinimidyl propionate, or N-hydroxysuccinimidyl butanoate, or N-hydroxysuccinimides such as PEG-NHS (Monfardini, C., et al., Bioconjugate Chem. 6 (1995) 62-69). In one embodiment the activated N-hydroxysuccinimide ester is using alkoxy-PEG-N-hydroxysuccinimide, such as methoxy-PEG-N-hydroxysuccinimide (MW 30000; Shearwater Polymers, Inc.), wherein R and m are as defined above. In one embodiment the PEG species is the N-hydroxysuccinimidyl ester of methoxy poly (ethylene glycol)-butyric acid. The term "alkoxy" refers to an alkyl ether group in which the term 'alkyl' means a straight-chain or branched-chain alkyl group containing a maximum of four carbon atoms, such as methoxy, ethoxy, n-propoxy and the like, preferably methoxy.

The term "substantially homogeneous form" as used within this application denotes that the PEGylated erythropoietins obtained, contained, or used are those having a defined number of PEG group attached. In one embodiment the PEGylated erythropoietin is a mono-PEGylated erythropoietin. The preparation may contain unreacted (i.e., PEG group lacking) erythropoietin, poly-PEGylated erythropoietin, as well as fragments of the polypeptide generated during the PEGylation reaction. The term "substantially homogeneous form" denotes that a preparation of a mono-PEGylated erythropoietin contains in one embodiment at least 50% (w/w) of the mono-PEGylated erythropoietin, at least 75% of the mono-PEGylated erythropoietin, at least 90% of the mono-PEGylated erythropoietin, or more than 95% of the mono-PEGylated erythropoietin. The percent values are based on the area-% of the chromatogram corresponding to the cation exchange chromatography purification from which the mono-PEGylated erythropoietin is obtained.

The current invention describes a method for the purification of a mono-PEGylated erythropoietin in order to obtain a substantially homogeneous form of a mono-PEGylated erythropoietin. It has surprisingly been found that the combination of two consecutive cation exchange chromatography steps both employing the same type of cation exchange material provides a substantially homogeneous form of a mono-PEGylated erythropoietin. Therefore the current invention provides a method for the purification of a mono-PEGylated erythropoietin comprising the steps of providing a solution comprising mono-, poly-, and not-PEGylated erythropoietin, performing two consecutive cation exchange chromatography steps, and recovering the purified mono-PEGylated erythropoietin in the second cation exchange chromatography step, wherein the same type of cation exchange material is used in both cation exchange chromatography steps. In one embodiment the recovering in the first cation exchange chromatography step is by a different elution method as the recovering in the second cation exchange chromatography step. In another embodiment is the cation exchange chromatography column regenerated after the first cation exchange chromatography step and after the second cation exchange chromatography step.

The recovery of the purified mono-PEGylated erythropoietin in the second cation exchange chromatography step is carried out by eluting the mono-PEGylated erythropoietin from the second cation exchange chromatography material. In one embodiment of the method according to the invention the two cation exchange chromatography steps differ in the elution method employed. The first cation exchange chromatography step in this embodiment is performed as a step elution method, i.e., the ionic strength of the used buffer is increased stepwise, i.e., at once, from one ionic strength value to the next ionic strength value, preferably by a change of 10% or more. The step elution method in one embodiment is performed as a three step elution method. In the first step mainly poly-PEGylated erythropoietin is eluted from the cation exchange chromatography column. The second increase in ionic strength basically elutes the mono-PEGylated erythropoietin with a purity of more than 60% based on the area of the corresponding size-exclusion chromatogram (area-%). The third increase in ionic strength mainly elutes the remaining not-PEGylated erythropoietin from the column.

The second cation exchange chromatography step is performed in one embodiment as a continuous elution method, i.e., the ionic strength of the buffer is increased continuously, preferably by a change of less than 5%. The eluted fractions containing the mono-PEGylated erythropoietin are combined in order to obtain a mono-PEGylated erythropoietin in substantially homogeneous form which in one embodiment contains less than 0.5% of low molecular weight forms based on the area of the corresponding chromatogram. The buffer is preferably present in a concentration of from 10 mM to 250 mM, in one embodiment of from 50 mM to 150 mM, in another embodiment at about 100 mM. Therefore in the method according to the invention are the two consecutive cation exchange chromatography steps the following steps:
a) applying an aqueous, buffered solution comprising a mixture of mono-, poly-, and non-PEGylated erythropoietin, and low molecular weight forms to a first cation exchange chromatography column under conditions suitable for binding of said mono-PEGylated erythropoietin to the cation exchange material contained in said first column,
b) recovering a mono-PEGylated erythropoietin from the first cation exchange chromatography column by a step elution method with a stepwise increase of the ionic strength of the flow through buffer, wherein the relative content of mono-PEGylated erythropoietin in the recovered solution is increased compared to the applied mixture of step a),
c) applying the recovered mono-PEGylated erythropoietin from step b) to a second cation exchange chromatography column under conditions suitable for binding of said mono-PEGylated erythropoietin to the cation exchange material contained in said second column, whereby the cation exchange material contained in said second column is of the same type as the cation exchange material in the first column, d) recovering the purified mono-PEGylated erythropoietin in a substantially homogeneous form from said second cation exchange chromatography column by a continuous elution method with a continuous increase of the ionic strength of the through flowing buffer.

Figure 1:
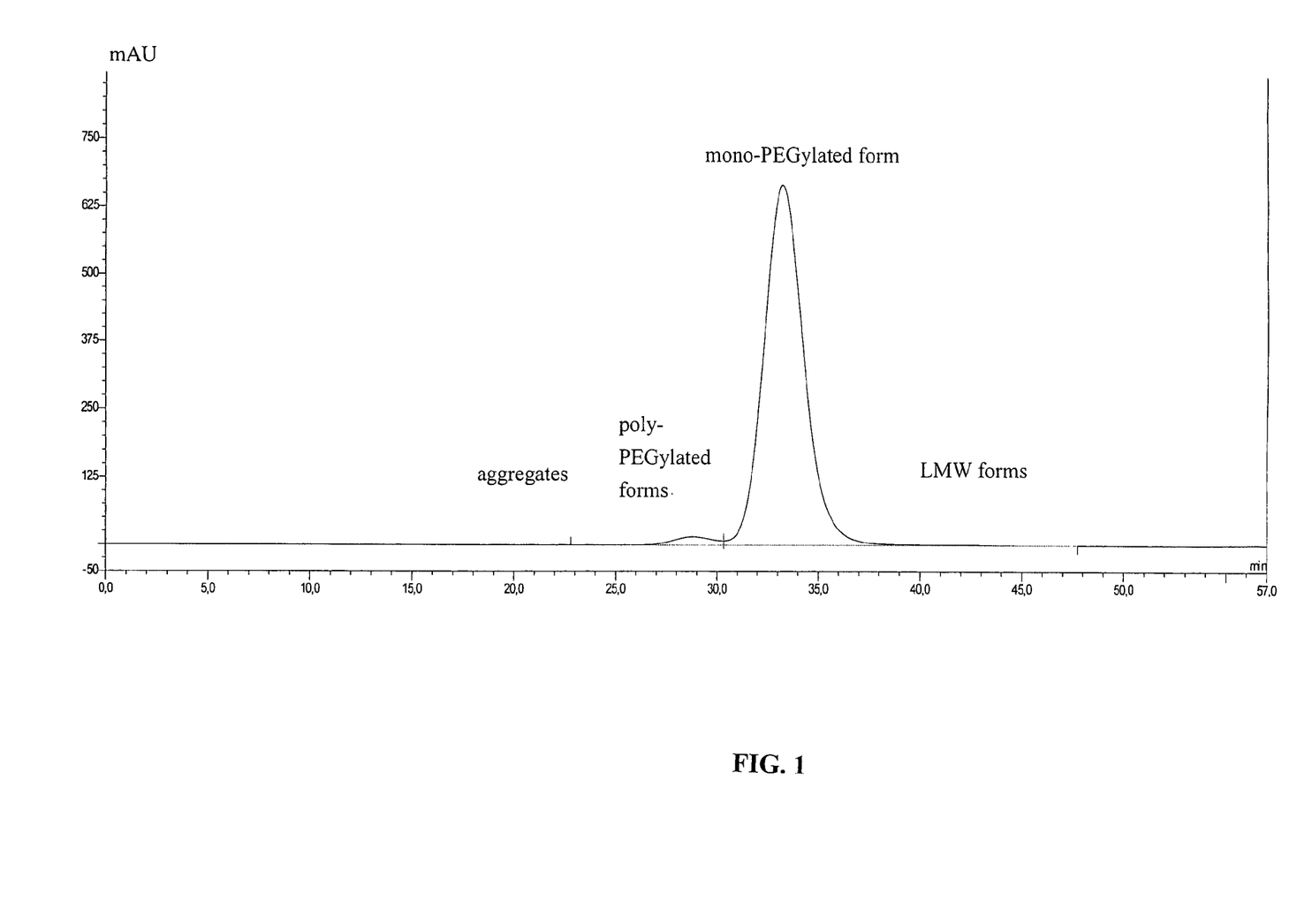
FIG. 1 SE-HPLC of a mixture of differently PEGylated erythropoietin including the correlation of peaks and substances.

The PEGylation of a polypeptide does not normally provide the PEGylation product in homogeneous form. It is obtained as a mixture of mono-PEGylated, poly-PEGylated, and non-PEGylated products. Therefore the solution of the PEGylated erythropoietin applied in step a) of the method is a mixture of mono-, poly-, and non-PEGylated erythropoietin and low molecular weight forms or fragments in an aqueous buffer. The relative content of the different substances is determined by size exclusion chromatography (SE-HPLC). An exemplary chromatogram is shown in FIG. 1. The sum of the area of the correlated peaks, i.e., the area under the peaks, in FIG. 1 is the total area of the size-exclusion chromatogram. The fraction of a single peak is given as area-%, i.e., as relative area fraction of the total area of the chromatogram.

General chromatographic methods, their use, and the related terms are known to a person skilled in the art. See for example, Chromatography, $5^{th}$ edition, Part A: Fundamentals and Techniques, Heftmann, E. (ed), Elsevier Science Publishing Company, New York, (1992) and other related textbooks. During the chromatography a buffer is flowing through the cation exchange chromatography column. This "flow through buffer" is adjusted according to the requirements of the steps of chromatography method. It transports the substance of interest to (applying) and from (eluting) the chromatographic material.

Figure 2:
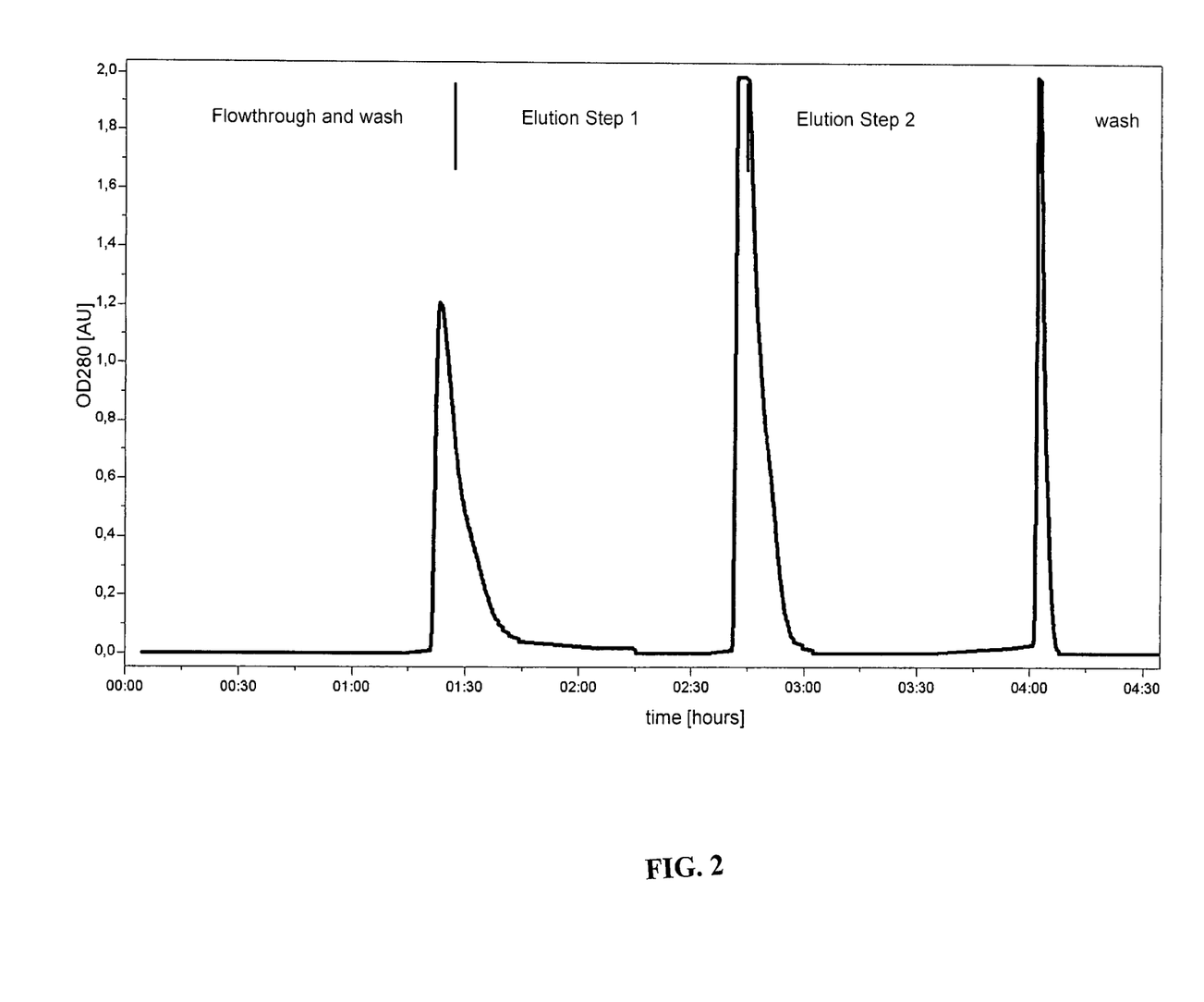
FIG. 2 Exemplary chromatogram of the step elution method.

In the first cation exchange chromatography step the mixture of mono-PEGylated, poly-PEGylated, and non-PEGylated erythropoietin is applied at a protein concentration of from 0.7 to 1.5 mg/ml, preferably about 1 mg/ml, to the first cation exchange chromatography column in an aqueous buffered solution. In one embodiment the aqueous buffered solution contains about 100 mM potassium phosphate at about pH 3.0. The term "about" as used within the current application denotes a range of 10% around the given value, i.e., ±10%. In a further embodiment, prior to and after the application the first column is washed with the same buffer solution. For the first step in the step elution method the buffer is changed to a buffer with about 100 mM potassium phosphate, about 90 mM sodium chloride at about pH 3.0. With this buffer hydrolyzed activated PEG reagent, i.e., the corresponding PEGylated carbonic acid, unreacted coupling reagent, and poly-PEGylated erythropoietin are eluted from the cation exchange chromatography column. For the second step in the three step elution method the buffer is changed to a buffer with about 100 mM potassium phosphate, about 250 mM sodium chloride at about pH 3.0. In this step the mono-PEGylated erythropoietin is recovered from the first cation exchange chromatography column. The collected through flowing buffer of this elution step is diluted approximately 1:5 (v/v) to 1:8 (v/v), preferably 1:5 (v/v), with purified water. An exemplary first cation exchange chromatography is shown in FIG. 2. For the third step in the three step elution method the buffer is changed to a buffer with about 100 mM potassium phosphate, about 750 mM sodium chloride at about pH 3.0. In this step not-PEGylated erythropoietin is recovered from the first cation exchange chromatography column.

The collected flow through buffer of the second step of the first cation exchange chromatography contains the mono-PEGylated erythropoietin in a relatively increased amount, i.e., the fraction by weight or by area-% (in the chromatogram of a size exclusion chromatography of the collected through flowing buffer of the second step) of the mono-PEGylated erythropoietin has increased when compared to that prior to the first cation exchange chromatography step. In one embodiment the relative content of mono-PEGylated erythropoietin is at least 60 area-%. In another embodiment, the relative content of mono-PEGylated erythropoietin is at least 80 area-%.

Figure 3:
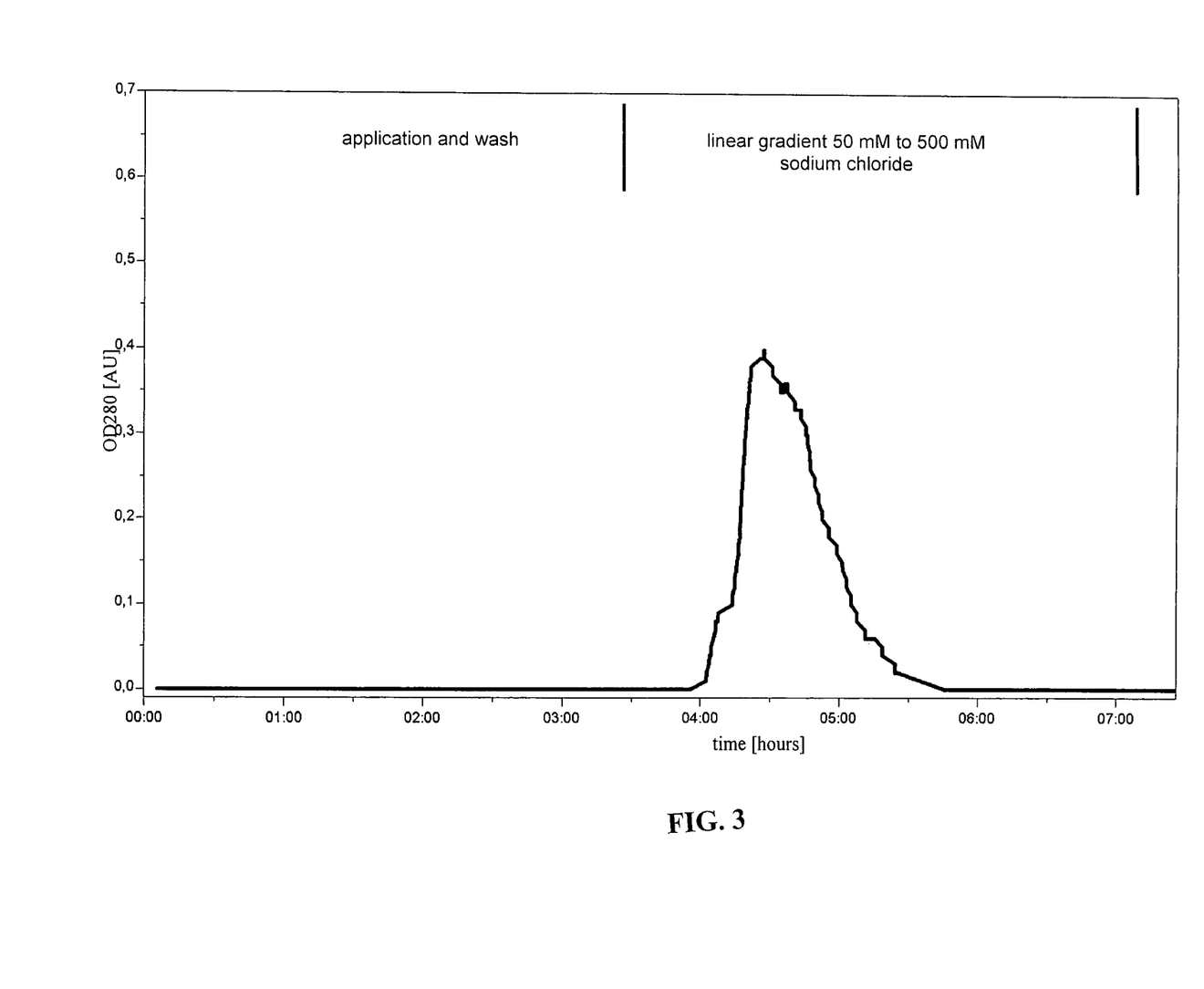
FIG. 3 Exemplary chromatogram of the continuous elution method.

For further purification of the mono-PEGylated erythropoietin a second cation exchange chromatography step is performed. For the second cation exchange chromatography the collected and diluted flow through buffer of the second elution step is adjusted to a potassium phosphate concentration of about 100 mM and to a pH of about pH 3.0 and is applied to a second cation exchange chromatography column containing a cation exchange material of the same type as the first cation exchange chromatography column. In one embodiment the second cation exchange column and the cation exchange material contained therein is the same as that in the first cation exchange chromatography step. The mono-PEGylated erythropoietin is recovered from the second cation exchange chromatography column by applying a linear gradient starting with potassium phosphate buffer of a concentration of about 100 mM with about 50 mM sodium chloride at about pH 3.0 and ending with a potassium phosphate buffer of a concentration of about 100 mM with about 500 mM sodium chloride at about pH 3.0. The change in the sodium chloride concentration is linear over ten column volumes. The flow through buffer is fractionated and each fraction is diluted with 1 M dipotassium hydrogen phosphate to increase the pH value to about pH 6 to 8. An exemplary chromatogram is shown in FIG. 3.

After the second cation exchange chromatography step the mono-PEGylated erythropoietin is obtained in substantially homogeneous form. In one embodiment, it has a purity of at least 95% by area.

A person of skill in the art is familiar with the technology of ion exchange chromatography. In the recovery step of the polypeptide bound to the cation exchange material the ionic strength, i.e., the conductivity, of the buffer/solution passing through the ion exchange column is increased. This can be accomplished either by an increased buffer salt concentration or by the addition of other salts, so called elution salts, to the buffer solution. Depending on the elution method the buffer/salt concentration is either increased at once (step elution method) or continuously (continuous elution method) by the fractional addition of a concentrated buffer or elution salt solution. Preferred elution salts are sodium citrate, sodium chloride, sodium sulphate, sodium phosphate, potassium chloride, potassium sulfate, potassium phosphate, or other salts of citric acid or phosphoric acid, or any mixture of these components. In one embodiment the elution salt is sodium citrate, sodium chloride, potassium chloride, or mixtures thereof.

In one embodiment of the current method the cation exchange material is a strong cation exchange material, preferably Toyopearl® SP 650 M. The concentration of the salt causing the elution, is, in one embodiment of the invention, in the range of from 5 mM to 500 mM, preferably in the range of from 5 mM to 400 mM, and more preferably in the range of from 5 mM to 250 mM. In another embodiment of the invention, the salt causing the elution is used at the same time as a buffer substance, such as citric acid or salts thereof or phosphoric acid or salts thereof.

The mono-PEGylated erythropoietin may be used in pharmaceutical compositions suitable for injection with a pharmaceutically acceptable carrier or vehicle by methods known in the art. For example, appropriate compositions have been described in WO 97/09996, WO 97/40850, WO 98/58660, and WO 99/07401. Among the preferred, pharmaceutically acceptable carriers for formulating the products of the invention are human serum albumin, human plasma proteins, etc. The compounds of the present invention may be formulated in 10 mM sodium/potassium phosphate buffer at pH 7 containing a tonicity agent, e.g., 132 mM sodium chloride. Optionally, the pharmaceutical composition may contain a preservative. The pharmaceutical composition may contain different amounts of mono-PEGylated erythropoietin, e.g., 10-1000 μg/ml, e.g., 50 μg or 400 μg.

Administration of the erythropoietin glycoprotein products of the present invention results in red blood cell formation in humans. Therefore, administration of the mono-PEGylated erythropoietin glycoprotein product replenishes this erythropoietin protein which is important in the production of red blood cells. The pharmaceutical compositions containing the mono-PEGylated erythropoietin glycoprotein products may be formulated at a strength effective for administration by various means to a human patient experiencing blood disorders characterized by low or defective red blood cell production, either alone or as part condition or disease. The pharmaceutical compositions may be administered by injection such as by subcutaneous or intravenous injection. Average quantities of the mono-PEGylated erythropoietin glycoprotein product may vary. The exact amount of conjugate is a matter of preference, subject to such factors as the exact type of condition being treated, the condition of the patient being treated, as well as the other ingredients in the composition. For example, 0.01 to 10 μg per kg body weight, preferably 0.1 to 1 μg per kg body weight, may be administered, e.g., once weekly.

The following examples, sequence listing and figures are provided to aid the understanding of the present invention, the true scope of which is set forth in the appended claims. It is understood that modifications can be made in the procedures set forth without departing from the spirit of the invention.

EXAMPLES

SE-HPLC

SE-HPLC separates proteins according to their apparent molecular weight. Therefore, the method is able to detect the presence of mono-PEGylated erythropoietin, low molecular weight forms and fragments, poly-PEGylated forms and higher aggregates of erythropoietin. The HPLC is equipped with a 220-nm detector and a Superose 6 HR column (dimensions 10×300 mm, Pharmacia Biotech, Cat-Nr: 17-0537-01) or a Superose 6 10/300 GL column (Pharmacia Biotech, Cat-Nr: 17-5172-01). The column is operated under isocratic conditions at room temperature, using a flow rate of about 0.4 ml/min. The mobile phase buffer is a 50 mM sodium phosphate buffer with 300 mM sodium chloride at pH 6.8. Dependent on the HPLC-system used, the method can be performed with a sample application volume of either 100 μL or 500 μL. The samples are diluted with the mobile phase buffer to a protein concentration of about 0.5 mg/mL (100 μL load) or 0.1 mg/mL (500 μL load). Samples with a protein concentration of less than 0.1 mg/mL can be used undiluted. The eluted proteins are detected at a detector wavelength of 220 nm.

Example 1

Fermentation and Purification of Erythropoietin

Erythropoietin can be produced, e.g., according to WO 01/87329, and purified as reported in WO 96/135718.

Example 2

PEGylation of Erythropoietin with Bifunctional Reagents a) Activation of Erythropoietin Specified amounts of a reagent containing a blocked thiol group, SATA (succinimidyl acetylthioacetate) or SATP (succinimidyl acetylthiopropionate) (dissolved in DMSO ad 10 mg/ml) were added to a solution of the benzyl protected erythropoietin, here to 1 ml of 5 mg/ml protein in 10 mM potassium phosphate buffer supplemented with 50 mM sodium chloride at pH 7.3. The reaction mixture was stirred for about 30 minutes (at 25° C.) and stopped by the addition of 1 M lysine solution to a final concentration of 10 mM. Excess amounts of SATA and SATP were removed by dialysis against 10 mM potassium phosphate buffer comprising 50 mM sodium chloride and 2 mM EDTA at pH 6.2. The protecting acetyl group was removed with hydroxylamine.

b) PEGylation of Activated Erythropoietin 380 mg methoxy-PEG-maleimide (MW 30.000; Shearwater Polymers, Inc., Huntsville (Ala. USA)) was dissolved in a solution containing 95 mg activated erythropoietin (4.5 mg/ml in 10 mM potassium phosphate buffer with 50 mM sodium chloride and 2 mM EDTA, pH 6.2). The resulting molar ratio between activated erythropoietin and methoxy-PEG-maleimide in the solution was 1:2 to 1:4. By the addition of 1 M aqueous hydroxylamine solution to a final concentration of 30 mM (pH 6.2) to the above solution the covalently linked blocked thiol groups of the activated erythropoietin were de-blocked. The resulting activated erythropoietin in the reaction mixture of the solution contained free thiol (—SH) groups. De-blocking of the thiol groups was followed immediately by the coupling reaction between the activated erythropoietin now containing free thiol (—SH) groups and methoxy-PEG-maleimide for 90 minutes (with stirring, at 25° C.). The coupling reaction was stopped by the addition of a 0.2 M aqueous cysteine solution to a final concentration of 2 mM to the reaction mixture. After 30 minutes, excess free thiol groups of the activated erythropoietin which did not react with methoxy-PEG-maleimide were blocked by the addition of a 0.5 M N-methylmaleimide solution in DMSO to reach a final concentration of 5 mM. After 30 minutes the resulting reaction mixture now containing PEGylated erythropoietin can be purified.

Example 3

Purification of Mono-PEGylated Erythropoietin a) First Chromatography on SP Toyopearl 650 M The first chromatography of the product was performed on a sulfopropyl (SP) column packed with SP Toyopearl 650M. The column was operated at room temperature. The maximum loading capacity of the first column was defined as 1.5 g protein per liter column volume (CV). The column was equilibrated with a 100 mM potassium phosphate buffer with pH 2.9 to 3.1 (SP-A buffer). After the loading step, the column was washed and eluted with a series of potassium phosphate buffers containing increasing amounts of NaCl. Hydrolyzed PEG reagent and poly-PEGylated forms were removed in the flow-through and the subsequent washing step with SP-A buffer and 100 mM potassium phosphate buffer, pH 2.9 to 3.1, containing 90 mM sodium chloride (SP-B buffer), respectively.

The mono-PEGylated erythropoietin was eluted by applying a 100 mM potassium phosphate buffer, pH 2.9 to 3.1, containing 250 mM sodium chloride (SP-C buffer), collected in a vessel and directly diluted 1:5 with purified water. This collected eluate is termed "SP eluate pool I".

The column was subsequently washed with 100 mM potassium phosphate buffer, pH 2.9 to 3.1, containing 750 mM sodium chloride (SP-D buffer) to remove unreacted erythropoietin and to regenerate the column.

b) Second Chromatography on SP Toyopearl 650 M

The second column was operated at room temperature. After equilibration with SP-A buffer the SP eluate pool I was applied to the column and the column was thereafter washed with SP-A buffer. The mono-PEGylated erythropoietin was eluted by applying a linear gradient with a slope of from 50 to 500 mM sodium chloride over ten column volumes buffered with 100 mM potassium phosphate buffer at pH 2.9 to 3.1. The product peak was fractionated in up to 8 single fractions and each fraction was directly diluted with 1 M dipotassium hydrogen phosphate to increase the pH to 6 to 8.

After the elution of mono-PEGylated erythropoietin was completed, the slope of the gradient can be increased leading to an immediate column wash with 100 mM potassium phosphate pH 2.9 to 3.1 containing 500 mM sodium chloride.

c) Regeneration of the SP Toyopearl 650 M Columns

The resins of both columns were regenerated in a sequence of seven steps. The columns were flushed with purified water followed by a 0.5 M sodium hydroxide solution. The alkaline solution was displaced with purified water followed by an acid wash (0.5 M sodium dihydrogen phosphate, 1 M phosphoric acid). After another purified water step, the columns were depyrogenated with 0.5 M sodium hydroxide for ≥4 hours. After caustic regeneration, the columns were washed with purified water again. See Table 1 and Table 2 for summary of column parameters.

TABLE 1

First chromatography column parameters

| Step | Buffer Solution | Column Volumes | Flow Rate [L/min] |
|---|---|---|---|
| Equilibration | 100 mmol/L potassium phosphate, pH 2.9-3.1 (SP-A buffer) | ≥6 | 1.6-2.1 |
| Column load | reaction mixture, diluted with SP-A (1:5) | n.a. | 1.6-2.1 |
| SP-A wash | 100 mmol/L potassium phosphate, pH 2.9-3.1 (SP-A buffer) | 2 | 1.6-2.1 |
| SP-B wash | 100 mmol/L potassium phosphate, pH 2.9-3.1, 90 mmol/L NaCl (SP-B buffer) | 2-3 | 1.6-2.1 |
| SP-C elution | 100 mmol/L potassium phosphate, pH 2.9-3.1, 250 mmol/L NaCl (SP-C buffer) | 2-3 | 1.6-2.1 |
| SP-D wash | 100 mmol/L potassium phosphate, pH 2.9-3.1, 750 mmol/L NaCl (SP-D buffer) | 2-3 | 1.6-2.1 |
| Rinse | PW III | ≥2 | 1.6-2.1 |
| Caustic column regeneration I | 0.5 mol/L NaOH | ≥2 | 1.6-2.1 |
| Rinse | PW III | ≥2 | 1.6-2.1 |
| Acid column regeneration | 1 mol/L phosphoric acid 0.5 mol/L sodium dihydrogen phosphate | ≥3 | 1.6-2.1 |
| Rinse | PW III | ≥2 | 1.6-2.1 |
| Caustic column regeneration II | 0.5 mol/L NaOH | ≥3 | n.a. |
| Rinse | PW III | ≥2 | 1.6-2.1 | n.a.: not applicable

TABLE 2

Second chromatography column parameters

| Step | Buffer Solution | Column Volumes | Flow Rate [L/min] |
|---|---|---|---|
| Equilibration | 100 mmol/L potassium phosphate, pH 2.9-3.1 (SP-A buffer) | ≥6 | 1.6-2.1 |
| Column load | SP eluate pool I, diluted with PW III (1:5) | n.a. | 1.6-2.1 |
| SP-A wash | 100 mmol/L potassium phosphate, pH 2.9-3.1, (SP-A buffer) | 2-3 | 1.6-2.1 |
| Gradient and elution | Gradient with a slope of 50-500 mmol/L NaCl over 10 CV between buffer SP-A and 100 mmol/L potassium phosphate, ' 500 mmol/L NaCl pH 2.9-3.1 (SP-E buffer) | 10 | 1.6-2.1 |
| Rinse | PW III | ≥2 | 1.6-2.1 |
| Caustic column regeneration I | 0.5 mol/L NaOH | ≥2 | 1.6-2.1 |
| Rinse | PW III | ≥2 | 1.6-2.1 |
| Acid column regeneration | 1 mol/L phosphoric acid 0.5 mol/L sodium dihydrogen phosphate | ≥3 | 1.6-2.1 |
| Rinse | PW III | ≥2 | 1.6-2.1 |
| Caustic column regeneration II | 0.5 mol/L NaOH | ≥3 | n.a. |
| Rinse | PW III | ≥2 | 1.6-2.1 | n.a.: not applicable

The invention claimed is:

1. A method for producing a mono-PEGylated erythropoietin comprising providing a solution comprising mono-, poly-, and non-PEGylated erythropoietin, performing two consecutive cation exchange chromatography steps, and recovering purified mono-PEGylated erythropoietin in the second cation exchange chromatography step,
wherein the same type of cation exchange material is used in both cation exchange chromatography steps,
wherein said two consecutive cation exchange chromatography steps comprise different elution methods,
wherein the first elution method is a step elution method and the second elution is a continuous elution method.

2. The method according to claim 1, wherein said two consecutive cation exchange chromatography steps comprise:
a) applying an aqueous, buffered solution comprising a mixture of mono-, poly-, non-PEGylated erythropoietin, and low molecular weight forms of erythropoietin to a first cation exchange chromatography column under conditions suitable for binding of any mono-PEGylated erythropoietin present in said aqueous buffered solution to the cation exchange material contained in said first column,
b) recovering any bound mono-PEGylated erythropoietin from the first cation exchange chromatography column by step elution with a stepwise increase of the ionic strength of flow through buffer to recover a mono-PEGylated erythropoietin fraction containing solution, wherein the fraction of said mono-PEGylated erythropoietin in the recovered solution is increased compared to the solution of step (a),
c) applying the recovered, mono-PEGylated erythropoietin of solution step b) to a second cation exchange chromatography column under conditions suitable for binding of said mono-PEGylated erythropoietin to the cation exchange material contained in said second column, wherein the cation exchange material contained in said second column is of the same type as the cation exchange material in the first column, and
d) recovering any mono-PEGylated erythropoietin bound to said second column, in a substantially homogeneous form by a continuous elution method with a continuous increase of the ionic strength of the through flowing buffer.

3. The method according to claim 2, wherein said stepwise increase of the ionic strength in step b) of the method is a three step ionic strength increase.

4. The method according to claim 3, comprising recovering the mono-PEGylated erythropoietin of step b) in the second step of the three step elution method.

5. The method according to claim 4, comprising recovering any poly-PEGylated erythropoietin of step b) after the first ionic strength increase of the through flowing buffer, recovering any mono-PEGylated erythropoietin after the second ionic strength increase of the through flowing buffer, and recovering any non-PEGylated erythropoietin after the third ionic strength increase of the through flowing buffer.

6. The method according to claim 2, wherein the difference of the concentration of the salt causing the elution in the step elution method of step b) is 120% or more in each of the steps of the step elution method.

7. The method according to claim 2, wherein said aqueous, buffered solution contains phosphoric acid or a salt thereof, citric acid or a salt thereof, or histidine or a salt thereof as a buffer substance.

8. The method according to claim 2, comprising recovering any mono-PEGylated erythropoietin of step d) from the second cation exchange chromatography column by applying a linear gradient, starting with potassium phosphate buffer at a concentration of about 100 mM with about 50 mM sodium chloride at about pH 3.0, and ending with a potassium phosphate buffer of a concentration of about 100 mM with about 500 mM sodium chloride at about pH 3.0, whereby the change in the sodium chloride concentration is linear over ten column volumes.

9. The method according to claim 2, wherein said aqueous buffered solution contains about 100 mM potassium phosphate buffer and has a pH of about 3.0.

10. The method according to claim 1, wherein said cation exchange material is a sulfopropyl cation exchange material.

11. The method according to claim 1, wherein the pH value of the solutions used in said chromatography step is about 3.0.

12. The method according to claim 1, wherein a salt causing elution of the PEGylated erythropoietin from the cation exchange chromatography columns is sodium citrate, sodium chloride, or potassium chloride.

13. The method according to claim 1, wherein said erythropoietin has the amino acid sequence of SEQ ID NO: 1 or SEQ ID NO: 2.

14. A method for production of a mono-PEGylated erythropoietin comprising:
a) PEGylating erythropoietin,
b) purifying a solution containing mono-PEGylated erythropoietin via two consecutive cation exchange chromatography steps, wherein said first and second cation exchange chromatography steps employ the same cation exchange material, and
c) recovering the mono-PEGylated erythropoietin from the second cation exchange chromatography column in a substantially homogeneous form, wherein said two consecutive cation exchange chromatography steps comprise different elution methods, wherein the first elution method is a step elution method and the second elution is a continuous elution method.

15. The method according to claim 14, the first cation exchange chromatograph step is carried out by using a first portion of the cation exchange material, and the second cationic exchange chromatograph step is carried out by using a second portion of the cation exchange material, wherein the cation exchange material used in the second cation exchange step is the same type of cation exchange material but is not the same portion of the cation exchange material used in the first cation exchange chromatography step.

16. The method according to claim 14, wherein said PEG residue is linear or branched, and has a molecular weight of 20-35 kDa as a linear molecule and 40 kDa as a branched molecule.

17. The method according to claim 14, wherein said mono-PEGylated erythropoietin is obtained in a substantially homogeneous form containing more than 95% by area of mono-PEGylated erythropoietin determined by size exclusion HPLC.

18. The method according to claim 14, comprising recovering said mono-PEGylated erythropoietin in the first cation exchange chromatography step, and said recovered mono-PEGylated erythropoietin has a purity of more than 60% by area determined by size exclusion HPLC.

* * * * *